United States Patent [19]

Baader et al.

[11] Patent Number: 4,946,841

[45] Date of Patent: Aug. 7, 1990

[54] PYRIDAZINE 3,5-DIHYDROXY CARBOXYLIC ACIDS AND DERIVATIVES THEREOF, THE USE THEREOF FOR HYPERCHOLESTEROLEMIA

[75] Inventors: Ekkehard Baader, Konigstein/Taunus; Heiner Jendralla, Frankfurt am Main; Bela Kerekjarto, Hofheim am Taunus; Gerhard Beck, Frankfurt am Main, all of Fed. Rep. of Germany

[73] Assignee: Hoechst Aktiengesellachaft, Frankfurt am Main, Fed. Rep. of Germany

[21] Appl. No.: 294,096

[22] Filed: Jan. 6, 1989

[30] Foreign Application Priority Data

Jan. 9, 1988 [DE] Fed. Rep. of Germany ....... 3800439
Jan. 14, 1988 [DE] Fed. Rep. of Germany ....... 3800785

[51] Int. Cl.$^5$ .................... A61K 31/50; C07D 237/06
[52] U.S. Cl. .................................. 514/247; 514/252; 544/224; 544/238
[58] Field of Search ...................... 544/238, 224, 238; 514/252, 247

[56] References Cited

U.S. PATENT DOCUMENTS

| | | | |
|---|---|---|---|
| 4,248,873 | 2/1981 | Bossert | 514/252 |
| 4,375,475 | 3/1983 | Willard | 549/292 |
| 4,540,796 | 9/1985 | Prugh | 549/292 |
| 4,613,610 | 9/1986 | Wareing | 514/406 |
| 4,647,576 | 3/1987 | Hoefle | 544/236 |
| 4,735,958 | 4/1988 | Roth | 514/314 |
| 4,761,419 | 8/1988 | Picard | 514/314 |

FOREIGN PATENT DOCUMENTS

86/00307  1/1986  World Int. Prop. O.

OTHER PUBLICATIONS

M. R. Boots et al., J. Pharm. Sci., vol. 69, No. 5 (1980), pp. 506–509.
F. M. Singer et al., Proc. Soc. Exper. Biol. Med., vol. 102 (1959), pp. 370–373.
H. Ferres et al., Tetrahedron letters, vol. 24, pp. 3769–3772 (1983).

Primary Examiner—Donald G. Daus
Attorney, Agent, or Firm—Finnegan, Henderson, Farabow, Garrett & Dunner

[57] ABSTRACT

New 3,5-dihydroxy carboxylic acids and derivatives thereof, a process for the preparation thereof, the use thereof as pharmaceuticals, pharmaceutical products and intermediates 3,5-Dihydroxy carboxylic acids and derivatives thereof, of the formula I

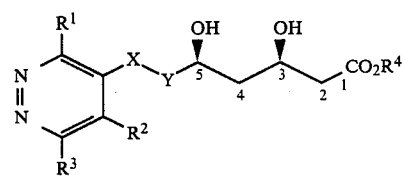

and the corresponding Lactones of the formula II

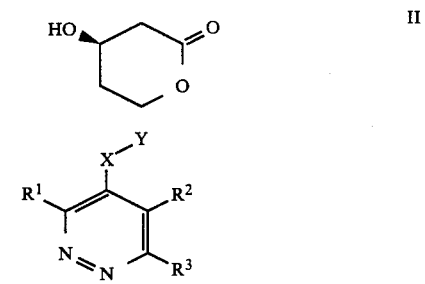

in which $R^1$, $R^2$, $R^3$, $R^4$ and X-Y have the indicated meanings, a process for the preparation of these compounds, the use thereof as pharmaceuticals, and pharmaceutical products are described. In addition, new intermediates for the preparation of the compounds of the formulae I and II are described.

6 Claims, No Drawings

PYRIDAZINE 3,5-DIHYDROXY CARBOXYLIC ACIDS AND DERIVATIVES THEREOF, THE USE THEREOF FOR HYPERCHOLESTEROLEMIA

DESCRIPTION

New 3,5-dihydroxy carboxylic acids and derivatives thereof, a process for the preparation thereof, the use thereof as pharmaceuticals, pharmaceutical products and intermediates.

The enzyme 3-hydroxy-3-methylglutaryl-coenzyme A reductase (HMG-CoA reductase) catalyzes the formation of mevalonic acid from 3-hydroxy-3-methylglutaryl-coenzyme A (HMG-CoA). This reaction plays a central part in the biosynthesis of cholesterol. Derivatives of 3-hydroxy-3-methylglutaric acid (HMG) and of mevalonic acid have been described as inhibitors of cholesterol biosynthesis (M. R. Boots et al., J. Pharm. Sci. 69, 306 (1980), F. M. Singer et al., Proc. Soc. Exper. Biol. Med. 102, 370 (1959), H. Feres, Tetrahedron Lett. 24, 3769 (1983)). 3-Hydroxy-3-methylglutaric acid itself shows a significant cholesterol-lowering action in the rat and in tests on humans (Z. Beg, Experientia 23, 380 (1967), ibid 24, 15 (1968), P. J. Lupien et al., Lancet 1978, 1, 283).

It has now been found that dihydroxy carboxylic acids of the general formula I, as well as the corresponding lactones of the formula II, are inhibitors of HMG-CoA reductase.

Hence the invention relates to 3,5-dihydroxy carboxylic acids and derivatives thereof, of the general formula I

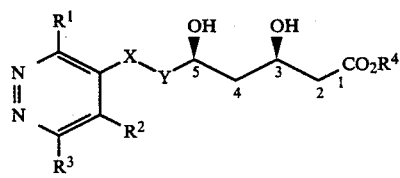

and the corresponding lactones of the formula II

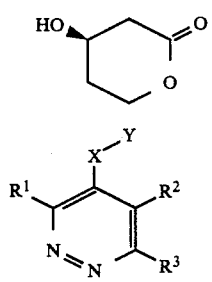

In the general formulae I and II,

X-Y denotes a radical of the formula —CH=CH— or —CH$_2$—CH$_2$—

$R^1$, $R^2$ and $R^3$ denote, independently of one another, hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3 to 6 carbon atoms, or denote a cyclic, saturated or up to doubly unsaturated hydrocarbon radical having 3 to 7 carbon atoms, an aromatic radical selected from the group comprising phenyl, furyl, thienyl and pyridyl, which can optionally carry in the nucleus 1 to 3 identical or different substituents from the following groups: halogen, trifluoromethyl, alkyl or alkenyl, having up to 6 carbon atoms in each case, hydroxyl, alkoxy having 1 to 6 carbon atoms, carboxyl or carbalkoxy having 1 to 6 carbon atoms in the alkoxy moiety, $R^4$ denotes hydrogen, a straight-chain or branched, saturated or unsaturated hydrocarbon radical having up to 8 carbon atoms, mono- or dihydroxyalkyl having 1 to 4 carbon atoms, a phenyl or benzyl radical whose nuclei can be substituted once or twice by halogen or an alkyl radical having 1 to 4 carbon atoms, or denotes alkali metal or an ammonium ion.

Preferred substituents $R^1$ and $R^2$ are a straight-chain or branched alkyl radical having 1 to 4 carbon atoms, a cycloalkyl radical having 5 to 6 carbon atoms, a cycloalkylmethyl or cycloalkenylmethyl radical having a ring size of 5 to 6 carbon atoms, a phenyl radical which can optionally carry 1 to 3 identical or different substituents from the following groups: halogen, trifluoromethyl, alkyl having 1 to 4 carbon atoms, hydroxyl, alkoxy having 1 to 4 carbon atoms or carbalkoxy having 1 to 4 carbon atoms in the alkoxy moiety.

Preferred meanings of $R^3$ are hydrogen, a straight-chain or branched alkyl or alkenyl radical having up to 6 carbon atoms, a cycloalkyl or cycloalkenyl radical each having 5 to 6 carbon atoms, a phenyl or pyridyl radical, it being possible for the aromatic radicals optionally to carry 1 to 3 identical or different substituents from the following groups: halogen, alkyl having 1 to 4 carbon atoms, hydroxyl, alkoxy having 1 to 4 carbon atoms or carbalkoxy having 1 to 4 carbon atoms in the alkoxy moiety.

Preferred radicals $R^4$ are hydrogen, methyl, ethyl, isopropyl, isobutyl, benzyl, sodium, potassium, ammonium (NH$_4$) or methyltris(hydroxymethyl)ammonium. Particularly preferred substituents $R^1$ are methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl and 4-trifluoromethylphenyl.

Particularly preferred substituents $R^2$ are methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl and 4-trifluoromethylphenyl.

Particularly preferred substituents $R^3$ are hydrogen, methyl, isopropyl, sec.-butyl, tert.-butyl, cyclohexyl, phenyl, 4-fluorophenyl, 2,5-dimethylphenyl, 3,5-dimethylphenyl and 4-trifluoromethylphenyl.

Particularly preferred substituents $R^4$ are hydrogen, methyl, ethyl, sodium and potassium.

The invention relates to the pure enantiomers as well as the racemates of the formula I and mixtures thereof, that is to say the racemates having the absolute configurations 3R/5S and 3S/5R for X-Y equal to HC=CH, and 3R/5R and 3S/5S for X-Y equal to CH$_2$—CH$_2$, as well as the pure enantiomers 3R/5S for X-Y equal to HC=CH, and 3R/5R for X-Y equal to CH$_2$—CH$_2$.

The invention furthermore relates to the pure enantiomers as well as the racemates of the general formula II derived from the abovementioned stereoisomeric open-chain dihydroxy carboxylic acids of the general formula I. Specifically, these are the racemates having the absolute configurations 3R/5S and 3S/5R for X-Y equal to HC=CH, and 3R/5R and 3S/5S for X-Y equal to CH$_2$—CH$_2$, as well as the pure enantiomers 3R/5S for X-Y equal to HC=CH and 3R/5R for X-Y equal to CH₂—CH₂.

The invention furthermore relates to a process for the preparation of the compounds of the general formulae I and II, which comprises (a) converting appropriately substituted aldehydes of the formula III

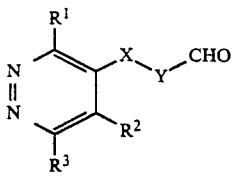

in which X-Y, R¹, R² and R³ have the indicated meanings into the corresponding hydroxy keto esters of the general formula IV

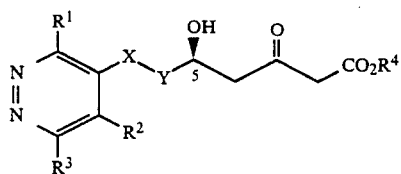

in which X-Y, R¹, R² and R³ have the indicated meanings, and R⁴ denotes alkyl having 1 to 8 carbon atoms, (b) converting the hydroxy keto esters of the formula IV into the corresponding 3,5-dihydroxy compounds of the formula I

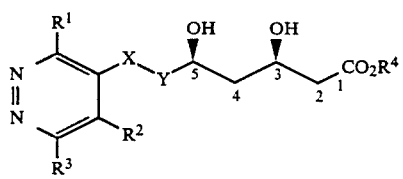

in which X-Y, R¹, R² and R³ have the meanings indicated for formula I, and R⁴ is alkyl having 1 to 8 carbon atoms, and hydrolyzing a resulting compound where appropriate to give a compound of the formula I in which R⁴ represents an alkal metal cation, liberating therefrom where appropriate the free acid (R⁴=hydrogen), and converting the free acid where appropriate into compounds of the formula I in which R⁴ has the meanings indicated for formula I with the exception of hydrogen, (c) and converting a resulting compound of formula I where appropriate into a lactone of the formula II

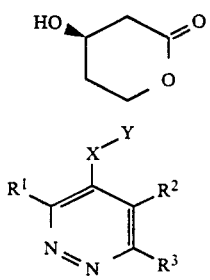

in which X-Y, R¹, R² and R³ have the indicated meanings, (d) and hydrogenating a resulting compound in which X-Y denotes the CH=CH group where appropriate to give a compound in which X-Y is the CH₂—CH₂ group.

Depending on the circumstances and requirements, the conversion of compounds of the formula III into compounds of the formula IV is carried out in a variety of versions such as, for example, 1. Reaction of the dianion of acetoacetic esters with aldehydes of the formula III in solvents such as THF at −78° C. to room temperature results in racemic compounds of the formula IV. Dianions of acetoacetic esters can be prepared with various bases, preferably sodium hydride and lithium diisopropylamide (LDA) preferably in THF at −40° C. to room temperature. 2. Reaction of the enolates of achiral acetic esters, such as, for example, ethyl or propyl esters, which are prepared with strong bases, preferably LDA, in THF, with aldehydes of the formula III in solvents such as, for example, THF at temperatures between −78° C. and 0° C. results in racemic compounds of the formula V,

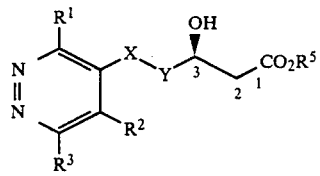

in which R⁵ denotes an achiral acid protective group such as, for example, the ethyl or propyl group. Reaction with another acetic ester enolate in solvents such as, for example, THF at −78° C. to room temperature results in racemic compounds of the formula IV.

3. Reaction of aldehydes of the formula III with lithium, sodium, potassium or magnesium enolates of optically active acetic esters in solvents such as THF at −78° C. to 0° C. results in optically active adducts of the formula V. In this case, R⁵ denotes a suitable optically active acid protective group which determines the stereochemistry at C-3. Preferably used for this is the group

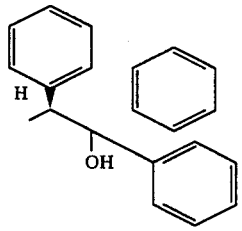

which, according to M. Braun and R. Devant (Tetrahedron Lett. 25, 5031 (1984)), yields the 3 R configuration and is prepared from L-(+)-mandelic acid. However, also suitable are other chiral optically active groups. The compounds of the formula V, which are now optically active, are converted with achiral acetic ester enolates as in version 2 into the compounds of the formula IV, which are now optically active, either directly or after conversion of the primary adducts into the corresponding alkyl esters, preferably methyl esters.

The conversion of compounds of the formula IV into compounds of the formula I is carried out, for example, in analogy to a process known from the literature (K. Narasaka and H. C. Pai, Chemistry Lett. 1980, 1415). Reaction is initially with a trialkylborane, preferably triethylborane, in THF at room temperature, followed by reduction with sodium borohydride, at −78° C. to 0° C., where appropriate with the addition of methanol. The stereochemical relationships described in the preceding statements are obtained in this way.

The racemic compounds of the formulae I and II can be separated into the pure enantiomers by the known processes of racemate resolution. The salts and acids of the compounds of the general formula I are obtained by the generally known methods.

The described process includes the preparation of the final products and intermediates with X-Y equal to $CH_2$—$CH_2$ and HC=CH. The hydrogenation of the double bond which is present where appropriate can be carried out, where appropriate, by customary processes either on intermediates or on the final products.

Compounds of the formula I in which X-Y is equal to $CH_2$—$CH_2$ are obtained, for example, by catalytic hydrogenation from compounds of the formula I with X-Y equal to CH=CH. The hydrogenation is carried out in solvents such as methanol, ethanol or ethyl acetate with catalysts such as Pd/C under atmospheric pressure or elevated pressure.

The lactones of the formula II are likewise obtained by processes known per se, for example by elimination of water from the open dihydroxy carboxylic acids of the formula I, $R^4$ equal to H, in benzene, hexane or toluene with the addition of p-toluenesulfonic acid at room temperature to the reflux temperature, or else from the open dihydroxy carboxylic esters of the formula I, for example $R^4$ equals methyl or ethyl in dichloromethane with the addition of, for example, trifluoroacetic acid at room temperature to the reflux temperature.

The aldehydes of the formula III are obtained, for example, from the nitriles of the formula VI

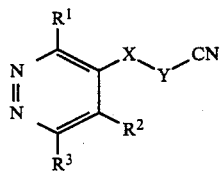

VI

The reaction of the nitriles of the formula VI in which X-Y, $R^1$, $R^2$ and $R^3$ have the meaning indicated for formula I with diisobutylaluminum hydride (DIBAH) in THF at −10° C. to 50° C. results, after hydrolysis, directly in the aldehydes of the formula III.

The nitriles of the formula VI are obtained from the aldehydes of the formula VII

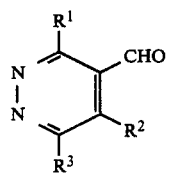

VII in which $R^1$, $R^2$ and $R^3$ have the indicated meaning, specifically and preferably by reaction with cyanomethanephosphonates, especially diisopropyl cyanomethanephosphonate, in solvents such as THF in the presence of a base, preferably sodium hydride at temperatures between −20° C. and room temperature. The E isomers are the predominant products.

The aldehydes of the formula VII are obtained by oxidation of the alcohols of the formula VIII,

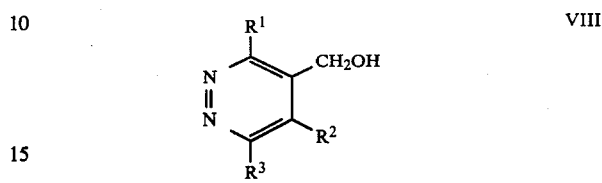

VIII in which $R^1$, $R^2$ and $R^3$ have the indicated meaning. The oxidation is preferably carried out with pyridinium chlorochromate (PCC) in dichloromethane at room temperature.

The alcohols of the formula VIII are produced by reduction from the esters of the formula IX,

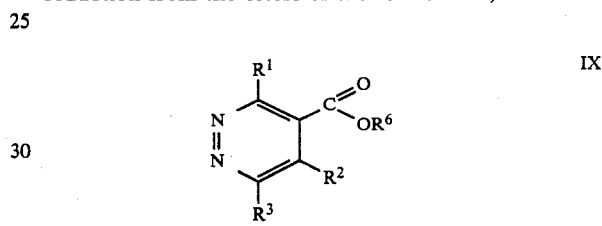

IX in which $R^1$, $R^2$ and $R^3$ have the indicated meanings. $R^6$ denotes a suitable acid protective group, preferably alkyl having 1 to 5 carbon atoms. The reduction to compounds of the formula VIII is preferably carried out with DIBAH in dichloromethane or lithium aluminum hydride in ether or THF at −40° C. to room temperature.

The pyridazinecarboxylic esters of the general formula IX in which $R^1$, $R^2$ and $R^3$ have a meaning given for the general formula I and which are used as starting material in the process according to the invention are obtained, for example, as depicted in scheme 1. Preparation is carried out by methods described in the literature or in analogy to such methods.

Scheme 1

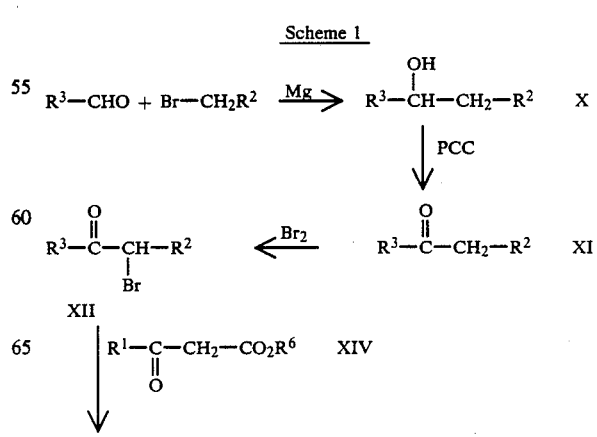

-continued
Scheme 1

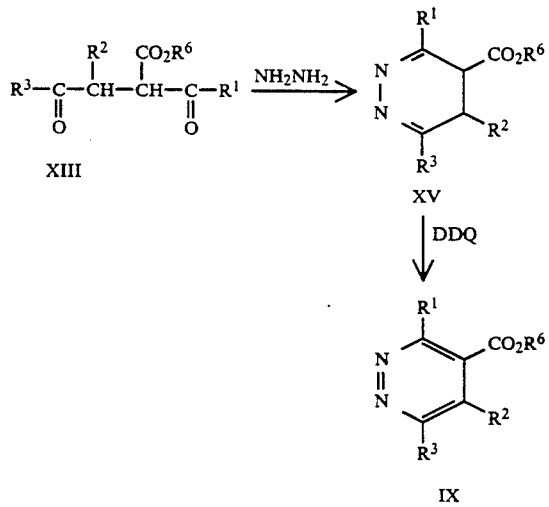

In analogy to the method described in Houben-Weyl, Methoden der organischen Chemie (Methods of organic chemistry) volume 6/1a/2, p. 928 (1980), for example, reaction of a Grignard reagent $R^2CH_2MgHal$ with an aldehyde $R^3$—CHO, where $R^2$ and $R^3$ have the indicated meaning, and Hal equal to chlorine, bromine and iodine, preferably chlorine, results in compounds of the formula X.

The alcohols of the formula X, where $R^2$ and $R^3$ have the indicated meaning, are oxidized by processes known from the literature give the ketones of the general formula XI, preferably with pyridinium chlorochromate (PCC) in dichloromethane at room temperature (E. J. Corey, Tetrahedron Lett. 1975, 2647).

The ketones of the formula XI are reacted with, for example, halogens such as chlorine, bromine or iodine, in organic solvents such as carbon tetrachloride, chloroform or dichloromethane, at temperatures between 0° C. and 40° C., to give the halogeno ketones of the general formula XII, where $R^2$ and $R^3$ have the indicated meaning. The reaction is preferably carried out with bromine in dichloromethane at room temperature.

The halogeno ketones of the general formula XII are converted into 1,4-diketones of the general formula XIII, where $R^1$, $R^2$, $R^3$ and $R^6$ have the indicated meaning, for example by reaction of β-keto esters of the general formula XIV, where $R^1$ and $R^6$ have the indicated meaning, with the halogeno ketones of the general formula XII.

The β-keto esters of the general formula XIV are prepared by methods known from the literature (for example in analogy to M. Jackman, M. Klenk, B. Fishburn, B. F. Tullar and S. Archer, J. Am. Chem. Soc. 70, 2884 (1948)). From these are obtained compounds in which $R^1$ has the meaning indicated above, and $R^6$ denotes a straight-chain or branched alkyl radical having up to 6 carbon atoms, preferably a methyl or ethyl radical.

The reaction to give the 1,4-diketone of the general formula XIII is carried out, for example, by forming the salt of the β-keto ester of the general formula XIV using bases such as, for example, sodium ethylate or sodium hydride (in situ) followed by a reaction with the halogeno ketone of the general formula XII at temperatures between 0° C. and 40° C., preferably 20° C., in a solvent such as, for example, diethyl ether, 1,2-dimethoxyethane, 1,2-diethoxyethane, tetrahydrofuran or mixtures of these solvents, preferably tetrahydrofuran.

Compounds of the formula XV in which $R^1$, $R^2$, $R^3$ and $R^6$ have the indicated meaning are preferably prepared by reacting the 1,4-diketone of the general formula XIII with hydrazine or hydrazine hydrate in a protic solvent such as methanol or ethanol, preferably ethanol, at temperatures between 0° C. and the boiling point of the solvent by processes known from the literature (T. L. Jacobs, Heterocyclic Compounds (Ed. R. C. Elderfield), Vol. 6, New York; J. Wiley & Sons 1957, p. 101 and literature cited therein).

Dehydrogenation to give compounds of the general formula IX in which $R^1$, $R^2$, $R^3$ and $R^6$ have the indicated meaning is preferably carried out with dehydrogenating agents such as, for example, 2,3-dichloro-5,6-dicyano-1, 4-benzoquinone or chloranil, as described by E. A. Braude, J. Hannah, R. Linstead, J. Chem. Soc. 1960, 3257.

The intermediates are purified, if necessary, by distillation, crystallization, flash chromatography or HPLC.

Biological test systems:

1. HMG-CoA reductase activity in enzyme preparations

The HMG-CoA reductase activity was measured on solubilized enzyme preparations from liver microsomes of rats which, after changing over the day/night rhythm, were induced with cholestyramine (®Cuemid).

The substrate used was (S,R)$^{14}$C-HMG-CoA, and the concentration of NADPH was maintained during the incubation by a regenerating system. $^{14}$C-mevalonate was removed from the substrate and other products (for example $^{14}$C-HMG) by column elution, with the elution profile of each individual sample being determined. $^3$H-mevalonate was not included in every test because the determination was of the relative inhibitory effect. In each series of tests, the enzyme-free control, the enzyme-containing normal mixture (=100%) and one with added product, final concentration $10^{-5}$ to $10^{-9}$M, were treated together. Each individual value was formed as the mean of 3 parallel samples. The significance of the differences between the means for product-free and product-containing samples was assessed by the t test.

The method described above was used to determine the figures for the inhibition of HMG-CoA reductase by the compounds according to the invention (IC$_{50}$/mol/liter signifies the molar concentration of the compound required for 50% inhibition):

IC$_{50}$ values between $1\times10^{-9}$ and $1\times10^{-8}$ were found for Examples 13b to k, and specifically $1.7\times10^{-9}$ for Example 13a, the compound being in racemic form. The IC$_{50}$ value of the compound from Example 19a is $1.3\times10^{-9}$.

2. Suppression or inhibition of HMG-CoA reductase in cell cultures of HEP-G2 cells Monolayers of HEP-G2 cells in lipoprotein-free nutrient medium were pre-incubated with appropriate concentrations of the test substances for a defined time (for example 1 hour) and, after addition of the labeled precursor, for example sodium $^{14}$C-acetate, incubation was continued (for example for 3 hours). After addition of an internal standard ($^3$H-cholesterol) a portion of the cells was hydrolyzed with alkali. The lipids from the hydrolyzed cells were extracted with chloroform/methanol.

This Lipid mixture was, after addition of carrier cholesterol, subjected to preparative thin-layer chromatography, the cholesterol band was visualized with iodine vapor and then isolated, and the amount of $^{14}C$-cholesterol formed from the $^{14}C$-precursor was determined by scintigraphy. Cellular protein was determined in an aliquot of the cells, so that it is possible to calculate the amount of $^{14}C$-cholesterol formed per unit time per mg of cellular protein. Comparison of this figure with the amount of $^{14}C$-cholesterol formed per mg of cellular protein and unit time in a culture treated in the same way but free of test substance yielded the inhibitory effect of the particular test product on cholesterol biosynthesis of HEP-G2 cell cultures.

Test of the inhibition of cholesterol biosynthesis in cell cultures by the substances confluent cell culture (monolayer) of HEP-G2 cells
1. Lipoprotein-free medium (DMEM)  24 h
2. Incubation with test products  1 h
3. Incubation with $^{14}C$-acetate  3 h
4. Cytolysis
5. TLC separation of the $^{14}C$-cholesterol reaction product
6. Isolation of the $^{14}C$-cholesterol
7. Scintillation measurement
8. Result
In mol $^{14}C$-cholesterol/mg of cellular protein by comparison with the solvent control The method described above was used to determine the figures for the inhibition of cholesterol biosynthesis (in HEP-G2 cells) by the compounds according to the invention (the $IC_{50}$/mol/liter is that concentration of the compound which brings about 50% inhibition of cholesterol biosynthesis).

The figures for this inhibition for the compounds of Examples 13b to k are between $10^{-7}$ and $10^{-9}$ mol per liter, and specifically are $5 \times 10^{-8}$ mol per liter for Example 13a and $2.5 \times 10^{-8}$ mol per liter for Example 19a.

The compounds of the general formula I or II are distinguished by strongly inhibiting HMB-CoA reductase, the rate-determining enzyme of cholesterol biosynthesis.

The extent of inhibition indicated by $IC_{50}$ values in the range $10^{-7}$ to $10^{-9}$ mol per liter for compounds of the general formula I or II is distinctly higher than for completely synthetic HMG-CoA reductase inhibitors known from the literature, such as, for example, those described by G. E. Stokker et al., J. Med. Chem. 29, 170 (1986).

The enzyme HMG-CoA reductase is widespread in nature. It catalyzes the formation of mevalonic acid from HMG-CoA. This reaction is a central step in cholesterol biosynthesis (cf. J. R. Sabine in CRC Series in Enzyme Biology: 3-hydroxy-3-methylglutaryl coenzyme A reductase, CRC Press Inc. Boca Raton, Fla. 1983 (ISBN 0-8493-6551-1)).

High cholesterol levels have been associated with a number of diseases such as, for example, coronary heart disease or arteriosclerosis. This is why lowering elevated cholesterol levels is an aim of therapy to prevent and treat such diseases.

One approach to this is to inhibit or reduce endogenous cholesterol biosynthesis. Inhibitors of HMG-CoA reductase block cholesterol biosynthesis at an early stage.

Hence the compounds of the general formula I or II are suitable as hypolipidemics and for the treatment and prophylaxis of arteriosclerotic changes.

Hence the invention also relates to pharmaceutical products based on these compounds, and to the use thereof as pharmaceuticals, especially as hypolipidemics and for the prophylaxis of arteriosclerotic changes.

Compounds of the formula I or II are used as hypolipidemics or antiarteriosclerotics in oral doses of 3 to 2,500 mg, but preferably in the dose range of 10 to 500 mg. These daily doses can, if required, also be divided into two to four single doses or administered in depot form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. Excretion of bile acids results in an increased de novo synthesis and thus in an increased breakdown of cholesterol (cf. M. S. Brown, P. T. Koranen and J. C. Goldstein, Science 212, 628 (1981); M. S. Brown and J. C. Goldstein, Spektrum der Wissenschaft 1985, 1, 96).

The compounds of the formula I or II, according to the invention, can be used in the form of the δ-lactones, as free acids or in the form of their physiologically acceptable inorganic or organic salts or as esters. Acids and salts or esters can be used in the form of their aqueous solutions or suspensions or else dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, or else polyethers such as, for example, polyethylene glycol, or else in the presence of other pharmacologically acceptable polymeric vehicles such as, for example, polyvinylpyrrolidone, or in solid formulations.

Preferred for the compounds of the formula I or II are solid presentations which can be administered orally and which may contain the customary auxiliaries. They are prepared by customary methods.

Formulations particularly suitable for oral use are tablets, coated tablets or capsules. One dosage unit preferably contains 10 to 500 mg of active substance.

The compounds of the formulae III, IV, V, VI, VII, VIII and IX are new and represent valuable intermediates for the preparation of compounds of the formula I. Hence the invention also relates to these compounds and to processes for the preparation thereof.

Prefatory note: NMR spectra were recorded in CDCl$_3$ with TMS internal standard, unless otherwise indicated. The following abbreviations are used to classify NMR signals: s=singlet, d=doublet, dd=doublet of doublets, tr=triplet, q=quartet, h=heptet, m=multiplet, br=broad. Melting points are uncorrected. The following abbreviations are used for substituents: i=iso, t=tertiary, c=cyclo.

EXAMPLE 1

General procedure for the preparation of compounds of the general formula X

Example 1a ($R^3 = R^2 = $ 4-fluorophenyl)

1,2-di(4-fluorophenyl)ethanol

Under a nitrogen atmosphere, 2.04 g (0.08 mol) of magnesium are covered with ether. 12.2 g (0.08 mol) of 4-fluorobenzyl chloride in 20 ml of ether are added dropwise to this in such a way that the ether boils gently. After addition is complete, the mixture is refluxed for a further 30 minutes, cooled to room temperature, and 8.3 g (0.07 mol) of 4-fluorobenzaldehyde in 20 ml of ether are slowly added dropwise. It may be necessary to cool with ice-water if the solution boils. After addition is complete, the mixture is left to reflux for 2 hours, then cooled and poured into 50 ml of ice-water. 50% concentrated hydrochloric acid is used to acidify, the phases are separated, and the aqueous phase is extracted 5 x with ether. The combined org. phases are neutralized with saturated sodium bicarbonate solution, washed with saturated sodium chloride solution, dried over magnesium sulfate and evaporated. The colorless oil crystallizes completely and yields 15.7 g of white crystals.

Melting point: 48°–50° C.

MS, $C_{14}H_{12}F_2O = 234$ (M+)

$^1$H NMR: $\delta$/ppm = 2.87 (d, 2H), 2.20 (s, br, 1H); 4.70 (tr, 1H); 6.8–7.3 (m, 8H).

The examples in Table 1 were prepared in analogy to Example 1a:

TABLE 1

$$\underset{R^3-CH-CH_2-R^2}{\overset{OH}{|}}$$

| Example | $R^2$ | $R^3$ |
|---------|-------|-------|
| 1 b | 4-FC$_6$H$_4$ | C$_6$H$_5$ |
| 1 c | C$_6$H$_5$ | C$_6$H$_5$ |
| 1 d | CH$_3$ | C$_6$H$_5$ |
| 1 e | 4-FC$_6$H$_4$ | i-C$_3$H$_7$ |
| 1 f | 4-FC$_6$H$_4$ | c-C$_6$H$_{11}$ |
| 1 g | i-C$_3$H$_7$ | C$_6$H$_5$ |
| 1 h | i-C$_3$H$_7$ | i-C$_3$H$_7$ |
| 1 i | 4-FC$_6$H$_4$ | C$_6$H$_5$ |
| 1 k | 4-C$_6$H$_4$CH$_3$ | 4-C$_6$H$_4$CH$_3$ |
| 1 l | 4-C$_6$H$_4$OCH$_3$ | 4-C$_6$H$_4$OCH$_3$ |
| 1 m | 4-FC$_6$H$_4$ | 4-FC$_6$H$_4$ |

EXAMPLE 2

General procedure for the preparation of compounds of the general formula XI

Example 2a ($R^3 = R^2 = $ 4-fluorophenyl) 4-Fluorobenzyl 4-fluorophenyl ketone Under a protective gas atmosphere, 7.8 g (36 mmol) of pyridinium chlorochromate are suspended in 80 ml of dichloromethane. To this are added, slowly at room temperature, 8.5 g (36 mmol) of the compound from Example a dissolved in 20 ml of dichloromethane. The reaction mixture is stirred at room temperature for 3 hours and then filtered through a silica gel column (solvent:ether) and evaporated. 6.4 g of white crystals result after recrystallization from methanol.

Melting point: 91°–93° C.

MS, $C_{14}H_{10}F_2O = 232$ (M+).

$^1$H-NMR: $\delta$/ppm = 4.27 (s, 2H); 6.87–7.47 (m, 6H); 7.90–8.23 (m, 2H).

The examples in the table were prepared in analogy to Example 2a

TABLE 2

$$\underset{R^3-\overset{\overset{\displaystyle O}{\|}}{C}-CH_2-R^2}{}$$

| Example | $R^2$ | $R^3$ | Mol. mass |
|---------|-------|-------|-----------|
| 2 b | 4-FC$_6$H$_4$ | C$_6$H$_5$ | C$_{14}$H$_{11}$FO 214[M+] |
| 2 c | C$_6$H$_5$ | C$_6$H$_5$ | C$_{14}$H$_{12}$O 196[M+] |
| 2 d | CH$_3$ | C$_6$H$_5$ | C$_9$H$_{10}$O 134[M+] |
| 2 e | 4-FC$_6$H$_4$ | i-C$_3$H$_7$ | C$_{11}$H$_{13}$FO 180[M+] |
| 2 f | 4-FC$_6$H$_4$ | c-C$_6$H$_{11}$ | C$_{14}$H$_{17}$FO 220[M+] |
| 2 g | i-C$_3$H$_7$ | C$_6$H$_5$ | C$_{11}$H$_{14}$O 162[M+] |
| 2 h | i-C$_3$H$_7$ | i-C$_3$H$_7$ | C$_8$H$_{16}$O 128[M+] |
| 2 i | 4-FC$_6$H$_4$ | C$_6$H$_5$ | C$_{14}$H$_{11}$FO 214[M+] |
| 2 k | 4-C$_6$H$_4$CH$_3$ | 4-C$_6$H$_4$CH$_3$ | C$_{16}$H$_{16}$O 224[M+] |
| 2 l | 4-C$_6$H$_4$OCH$_3$ | 4-C$_6$H$_4$OCH$_3$ | C$_{16}$H$_{16}$O$_3$ 256[M+] |
| 2 m | 4-FC$_6$H$_4$ | 4-FC$_6$H$_4$ | C$_{14}$H$_{10}$F$_2$O 232[M+] |

EXAMPLE 3

General procedure for the preparation of compounds of the general formula XII

Example 3a ($R^3 = R^2 = $ 4-fluorophenyl)
α-Bromo-α-(4-fluorophenyl)-4-fluoroacetophenone At room temperature, 1.5 g (6.5 mmol) of the compound from Example 2a are dissolved in 20 ml CHCl$_3$, and 1/10 of 3.34 ml (6.5 mmol) of bromine is added (a dark orange color is produced). The resulting solution is cautiously heated until the solution becomes yellow in color and is then cooled to 0° C. The remaining bromine is added, and the reaction mixture is stirred at room temperature for 16 hours. The orange solution is extracted 3 x with saturated NaHCO$_3$ solution and then washed once with saturated sodium chloride solution. Drying of the magnesium sulphate followed by concentration results in an orange oil which partially crystallizes. The product (1.9 g) is obtained as a white powder by crystallization from ethanol.

Melting point: 75°–78° C.

MS, $C_{14}H_9BrF_2O = 310/312$ (M+).

$^1$H-NMR: $\delta$/ppm = 6.9–8.0 (m,9H).

The examples in Table 3 were prepared in analogy to Example 3a.

TABLE 3

$$\underset{R^3-\overset{\overset{\displaystyle O}{\|}}{C}-\underset{\underset{\displaystyle Br}{|}}{CH}-R^2}{}$$

| Example | $R^2$ | $R^3$ | Mol. mass |
|---------|-------|-------|-----------|
| 3 b | 4-FC$_6$H$_4$ | C$_6$H$_5$ | C$_{14}$H$_{10}$BrFO 292/294[M+] |
| 3 c | C$_6$H$_5$ | C$_6$H$_5$ | C$_{14}$H$_{12}$BrO 274/276[M+] |

TABLE 3-continued $$R^3-\overset{\overset{O}{\|}}{C}-\underset{\underset{Br}{|}}{CH}-R^2$$

| Example | $R^2$ | $R^3$ | Mol. mass |
|---|---|---|---|
| 3 d | $CH_3$ | $C_6H_5$ | $C_9H_9BrO$ |
| 3 e | $4\text{-}FC_6H_4$ | $i\text{-}C_3H_7$ | $C_{11}H_{12}BrFO$ 258/260[M+] |
| 3 f | $4\text{-}FC_6H_4$ | $c\text{-}C_6H_{11}$ | $C_{14}H_{16}BrFO$ 298/300[M+] |
| 3 g | $i\text{-}C_3H_7$ | $C_6H_5$ | $C_{11}H_{13}BrO$ 240/242[M+] |
| 3 h | $i\text{-}C_3H_7$ | $i\text{-}C_3H_7$ | $C_8H_{15}BrO$ 206/208[M+] |
| 3 i | $4\text{-}FC_6H_4$ | $C_6H_5$ | $C_{16}H_{10}BrFO$ 292/294[M+] |
| 3 k | $4\text{-}C_6H_4CH_3$ | $4\text{-}C_6H_4CH_3$ | $C_{14}H_{15}BrO$ 302/304[M+] |
| 3 l | $4\text{-}C_6H_4OCH_3$ | $4\text{-}C_6H_4OCH_3$ | $C_{16}H_{15}BrO_3$ 334/336[M+] |
| 3 m | $4\text{-}FC_6H_4$ | $4\text{-}FC_6H_4$ | $C_{14}H_9BrF_2O$ 310/312[M+] |

EXAMPLE 4
General procedure for the preparation of compounds of the general formula XIII

Example 4a ($R^3=R^2=$4-fluorophenyl, $R^1=i\text{-}C_3H_7$, $R^6=C_2H_5$)

Ethyl 2-(α-4-fluorobenzoyl-4-fluorobenzyl)-3-oxo-4,4-dimethylpentanoate

Under an atmosphere of dry nitrogen, 0.2 g (8 mmol) of sodium hydride (60% in liquid paraffin) in a flask is washed 2 x with n-heptane and suspended in 20 ml of dry tetrahydrofuran. To this is added dropwise, at 0° C., 0.8 g (5.1 mmol) of ethyl isopropylacetoacetate (XIV) in ml of THF. After the addition, the mixture is stirred at 0° C. for 15 minutes (the solution becomes clear). Then, at 0° C. 1.5 g (4.8 mmol) of the compound from Example 3a, dissolved in 5 ml of abs. THF, are slowly added, and the mixture is stirred at room temperature for 21 hours.

The reaction mixture is concentrated, the residue is taken up in ether, and the solution is washed 2 x with saturated sodium bicarbonate and 1 x with saturated sodium chloride solution, dried over magnesium sulfate and evaporated. The resulting yellow oil (1.4 g) is used directly in the next stage (Example 5a).

MS, $C_{22}H_{22}F_2O_4=389$ (M+H+)

The example in Table 4 were prepared in analogy to Example 4a and using the appropriate $R^1$-substituted ethyl acetoacetate XIV

TABLE 4

$$R^3-\overset{\overset{O}{\|}}{C}-\underset{\underset{}{|}}{\overset{\overset{R^2}{|}}{CH}}-\underset{\underset{}{|}}{\overset{\overset{CO_2R^6}{|}}{CH}}-\overset{\overset{}{\|}}{\underset{O}{C}}-R^1$$

| Example | $R^1$ | $R^2$ | $R^3$ | $R^6$ |
|---|---|---|---|---|
| 4 b | $CH_3$ | $4\text{-}FC_6H_4$ | $C_6H_5$ | $C_2H_5$ |
| 4 c | $CH_3$ | $C_6H_5$ | $C_6H_5$ | $C_2H_5$ |
| 4 d | $i\text{-}C_3H_7$ | $CH_3$ | $C_6H_5$ | $C_2H_5$ |
| 4 e | $i\text{-}C_3H_7$ | $4\text{-}FC_6H_4$ | $i\text{-}C_3H_7$ | $C_2H_5$ |
| 4 f | $i\text{-}C_3H_7$ | $4\text{-}FC_6H_4$ | $c\text{-}C_6H_{11}$ | $C_2H_5$ |
| 4 g | $4\text{-}FC_6H_4$ | $i\text{-}C_3H_7$ | $C_6H_5$ | $C_2H_5$ |
| 4 h | $4\text{-}FC_6H_4$ | $i\text{-}C_3H_7$ | $i\text{-}C_3H_7$ | $C_2H_5$ |
| 4 i | $t\text{-}C_4H_9$ | $4\text{-}FC_6H_4$ | $C_6H_5$ | $C_2H_5$ |
| 4 k | $i\text{-}C_3H_7$ | $4\text{-}C_6H_4CH_3$ | $4\text{-}C_6H_4CH_3$ | $C_2H_5$ |
| 4 l | $i\text{-}C_3H_7$ | $4\text{-}C_6H_4OCH_3$ | $4\text{-}C_6H_4OCH_3$ | $C_2H_5$ |
| 4 m | $CH_3$ | $4\text{-}FC_6H_4$ | $4\text{-}FC_6H_4$ | $C_2H_5$ |

EXAMPLE 5
General procedure for the preparation of compounds of the general formula XV

Example 5a ($R^3=R^2=$4-fluorophenyl, $R^1=i\text{-}C_3H_7$, $R^6=C_2H_5$)

Ethyl 3,4-di (4-fluorophenyl)-6-isopropyl-4,5-dihydropyridazine-5-carboxylate

Under a nitrogen atmosphere, 1.43 g (3.7 mmol) of the compound from Example 4a are dissolved in 10 ml of ethanol and cooled to 0° C. At this temperature, 0.2 ml (3.7 mmol) of hydrazine hydrate is slowly added dropwise. The mixture is allowed to reach room temperature and is stirred for 1 hour. The reaction solution is evaporated. Flash chromatography on silica gel (cyclohexane/ethyl acetate 3/1) yields 0.31 g of the title compound as a colorless oil.

The compound of the formula XV is used directly in the next stage without further characterization (Example 6a).

MS, $C_{22}H_{22}F_2N_2O_2=385$ (M+H+).

The examples in Table 5 were prepared in analogy to Example 5a

TABLE 5

| Example | $R^1$ | $R^2$ | $R^3$ | $R^6$ |
|---|---|---|---|---|
| 5 b | $CH_3$ | $4\text{-}FC_6H_4$ | $C_6H_5$ | $C_2H_5$ |
| 5 c | $CH_3$ | $C_6H_5$ | $C_6H_5$ | $C_2H_5$ |
| 5 d | $i\text{-}C_3H_7$ | $CH_3$ | $C_6H_5$ | $C_2H_5$ |
| 5 e | $i\text{-}C_3H_7$ | $4\text{-}FC_6H_4$ | $i\text{-}C_3H_7$ | $C_2H_5$ |
| 5 f | $i\text{-}C_3H_7$ | $4\text{-}FC_6H_4$ | $c\text{-}C_6H_{11}$ | $C_2H_5$ |
| 5 g | $4\text{-}FC_6H_4$ | $i\text{-}C_3H_7$ | $C_6H_5$ | $C_2H_5$ |
| 5 h | $4\text{-}FC_6H_4$ | $i\text{-}C_3H_7$ | $i\text{-}C_3H_7$ | $C_2H_5$ |
| 5 i | $t\text{-}C_4H_9$ | $4\text{-}FC_6H_4$ | $C_6H_5$ | $C_2H_5$ |
| 5 k | $i\text{-}C_3H_7$ | $4\text{-}C_6H_4CH_3$ | $4\text{-}C_6H_4CH_3$ | $C_2H_5$ |
| 5 l | $i\text{-}C_3H_7$ | $4\text{-}C_6H_4OCH_3$ | $4\text{-}C_6H_4OCH_3$ | $C_2H_5$ |
| 5 m | $CH_3$ | $4\text{-}FC_6H_4$ | $4\text{-}FC_6H_4$ | $C_2H_5$ |

EXAMPLE 6

General procedure for the preparation of compounds of the general formula IX

Example 6a ($R^3 = R^2 =$ 4-fluorophenyl, $R^1 =$ i-$C_3H_7$, $R^6 = C_2H_5$)

Ethyl 3,4-di(4-fluorophenyl)-6-isopropylpyridazine-5-carboxylate

Under a nitrogen atmosphere, 260 mg (0.7 mmol) of the compound from Example 5a and 170 mg (0.7 mmol) of dichlorodicyanobenzoquinone are introduced into 25 ml of toluene and stirred at 50° C. for 3 hours.

The reaction mixture is concentrated and filtered through a silica gel column (cyclohexane/ethyl acetate 3/1). The product (166 mg) crystallizes out.

Melting point: 103° C.

MS, $C_{22}H_{20}F_2N_2O_2 = 382$ (M+)

$^1$H-NMR: $\delta$/ppm = 1.00 (tr,J = 7 Hz,3H); 1.50 (d,J = 7 Hz,6H); 3.23 (h,1H), 4.13 (q,J = 7 Hz,2H); 6.90–7.53 (m,8H).

The examples in Table 6 were obtained in analogy to Example 6a.

TABLE 6

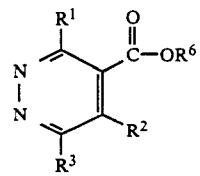

| Example | $R^1$ | $R^2$ | $R^3$ | $R^6$ | Mol. mass |
|---|---|---|---|---|---|
| 6 b | $CH_3$ | 4-$FC_6H_4$ | $C_6H_5$ | $C_2H_5$ | $C_{20}H_{17}FN_2O_2$ 336[M+] |
| 6 c | $CH_3$ | $C_6H_5$ | $C_6H_5$ | $C_2H_5$ | $C_{20}H_{18}N_2O_2$ 318[M+] |
| 6 d | i-$C_3H_7$ | $CH_3$ | $C_6H_5$ | $C_2H_5$ | $C_{17}H_{20}N_2O_2$ 284[M+] |
| 6 e | i-$C_3H_7$ | 4-$FC_6H_4$ | i-$C_3H_7$ | $C_2H_5$ | $C_{19}H_{23}FN_2O_2$ 330[M+] |
| 6 f | i-$C_3H_7$ | 4-$FC_6H_4$ | c-$C_6H_{11}$ | $C_2H_5$ | $C_{22}H_{27}FN_2O_2$ 370[M+] |
| 6 g | 4-$FC_6H_4$ | i-$C_3H_7$ | $C_6H_5$ | $C_2H_5$ | $C_{22}H_{21}FN_2O_2$ 364[M+] |
| 6 h | 4-$FC_6H_4$ | i-$C_3H_7$ | i-$C_3H_7$ | $C_2H_5$ | $C_{19}H_{23}FN_2O_2$ 330[M+] |
| 6 i | t-$C_4H_9$ | 4-$FC_6H_4$ | $C_6H_5$ | $C_2H_5$ | $C_{23}H_{23}FN_2O_2$ 378[M+] |
| 6 k | i-$C_3H_7$ | 4-$C_6H_4CH_3$ | 4-$C_6H_4CH_3$ | $C_2H_5$ | $C_{24}H_{26}N_2O_2$ 374[M+] |
| 6 l | i-$C_3H_7$ | 4-$C_6H_4OCH_3$ | 4-$C_6H_4OCH_3$ | $C_2H_5$ | $C_{24}H_{26}N_2O_4$ 406[M+] |
| 6 m | $CH_3$ | 4-$FC_6H_4$ | 4-$FC_6H_4$ | $C_2H_5$ | $C_{20}H_{16}F_2N_2O_2$ 354 [M+] |

EXAMPLE 7

General procedure for the preparation of compounds of the general formula VIII

Example 7a ($R^1 =$ i-$C_3H_7$, $R^2 =$ 4-$FC_6H_4$, $R^3 = FC_6H_4$)

3,4-Di(4-fluorophenyl)-6-isopropylpyridazin-5-ylmethanol 15.4 ml (18.5 mmol) of diisobutylaluminum hydride solution (toluene) are added dropwise, at −78° C. under argon, to 2.4 g (6.2 mmol) of the compound from Example 6a in 230 ml of dichloromethane. The mixture is stirred at 0° C. for 4 h, 1 ml of methanol is added, and the mixture is diluted with water and ether until the phases separate. The organic phase is separated off, the aqueous phase is extracted once more with ether, and the combined organic extracts are washed with saturated sodium chloride solution (2 x). After drying with magnesium sulfate, the solvent is removed in vacuo. The resulting alcohol 7a (1.9 g) is used for the next stage without further purification.

Oil.

MS, $C_{20}H_{18}F_2N_2O = 340$ (M+).

$^1$H-NMR $\delta$/ppm = 1.50 (d,J = 7 Hz,6H); 3.63 (h,1H); 4.60 (s,2H); 6.73–7.43 (m,8H).

The examples in Table 7 were obtained in analogy to Example 7a.

TABLE 7

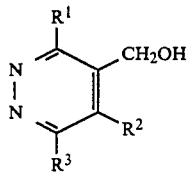

| Example | $R^1$ | $R^2$ | $R^3$ | Mol. mass |
|---|---|---|---|---|
| 7 b | $CH_3$ | 4-$FC_6H_4$ | $C_6H_5$ | $C_{18}H_{15}FN_2O$ 294[M+] |
| 7 c | $CH_3$ | $C_6H_5$ | $C_6H_5$ | $C_{18}H_{10}N_2O$ 276[M+] |
| 7 d | i-$C_3H_7$ | $CH_3$ | $C_6H_5$ | $C_{15}H_{18}N_2O$ 242[M+] |
| 7 e | i-$C_3H_7$ | 4-$FC_6H_4$ | i-$C_3H_7$ | $C_{17}H_{21}FN_2O$ 288[M+] |
| 7 f | i-$C_3H_7$ | 4-$FC_6H_4$ | c-$C_6H_{11}$ | $C_{20}H_{25}FN_2O$ 328[M+] |
| 7 g | 4-$FC_6H_4$ | i-$C_3H_7$ | $C_6H_5$ | $C_{20}H_{19}FN_2O$ 322[M+] |
| 7 h | 4-$FC_6H_4$ | i-$C_3H_7$ | i-$C_3H_7$ | $C_{17}H_{21}FN_2O$ 288[M+] |
| 7 i | t-$C_4H_9$ | 4-$FC_6H_4$ | $C_6H_5$ | $C_{21}H_{21}FN_2O$ 336[M+] |

TABLE 7-continued

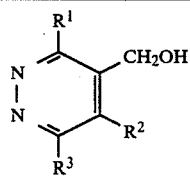

| Example | R$^1$ | R$^2$ | R$^3$ | Mol. mass |
|---|---|---|---|---|
| 7 k | i-C$_3$H$_7$ | 4-C$_6$H$_4$CH$_3$ | 4-C$_6$H$_4$CH$_3$ | C$_{22}$H$_{24}$N$_2$O 332[M$^+$] |
| 7 l | i-C$_3$H$_7$ | 4-C$_6$H$_4$OCH$_3$ | 4-C$_6$H$_4$OCH$_3$ | C$_{22}$H$_{24}$N$_2$O$_4$ 364 [M$^+$] |
| 7 m | CH$_3$ | 4-FC$_6$H$_4$ | 4-FC$_6$H$_4$ | C$_{18}$H$_{14}$F$_2$N$_2$O 312 [M$^+$] |

EXAMPLE 8

General procedure for the preparation of compounds of the general formula VII

Example 8a (R$^1$=i-C$_3$H$_7$, R$^2$=4-FC$_6$H$_4$, R$^3$=4-FC$_6$H$_4$)
3,4-Di(4-fluorophenyl)-6-isopropylpyridazine-5-carbaldehyde 1.8 g (5.5 mmol) of the compound from Example 7a in 30 ml of dichloromethane are poured into a suspension of 1.8 g (0.4 mmol) of PCC in 30 ml of dichloromethane at room temperature. After stirring at room temperature for 3 h, 3 volumes of ether are added, and the mixture is filtered through silica gel. Removal of the solvent in vacuo, and chromatography on silica gel (cyclohexane/ethyl acetate 1) yields 1.5 g of the title compound as a solid.

Melting point: 136° C.
MS, C$_{20}$H$_{16}$F$_2$N$_2$O=338 (M$^+$)
$^1$H-NMR: δ/ppm=1.47 (d,j=7 Hz,6H); 3.73 (h,1H); 6.83-7.50 (m,8H); 10.00 (s,1H).

The examples in Table 8 were obtained in analogy to Example 8a.

TABLE 8

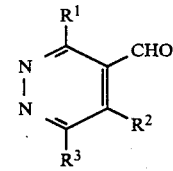

| Example | R$^1$ | R$^2$ | R$^3$ | Mol. mass |
|---|---|---|---|---|
| 8 b | CH$_3$ | 4-FC$_6$H$_4$ | C$_6$H$_5$ | C$_{18}$H$_{13}$FN$_2$O 292[M$^+$] |
| 8 c | CH$_3$ | C$_6$H$_5$ | C$_6$H$_5$ | C$_{18}$H$_{14}$N$_2$O 274[M$^+$] |
| 8 d | i-C$_3$H$_7$ | CH$_3$ | C$_6$H$_5$ | C$_{15}$H$_{16}$N$_2$O 240[M$^+$] |
| 8 e | i-C$_3$H$_7$ | 4-FC$_6$H$_4$ | i-C$_3$H$_7$ | C$_{17}$H$_{19}$FN$_2$O 286[M$^+$] |
| 8 f | i-C$_3$H$_7$ | 4-FC$_6$H$_4$ | c-C$_6$H$_{11}$ | C$_{20}$H$_{23}$FN$_2$O 326[M$^+$] |
| 8 g | 4-FC$_6$H$_4$ | i-C$_3$H$_7$ | C$_6$H$_5$ | C$_{20}$H$_{17}$FN$_2$O 320[M$^+$] |
| 8 h | 4-FC$_6$H$_4$ | i-C$_3$H$_7$ | i-C$_3$H$_7$ | C$_{17}$H$_{19}$FN$_2$O 286[M$^+$] |
| 8 i | t-C$_4$H$_9$ | 4-FC$_6$H$_4$ | C$_6$H$_5$ | C$_{21}$H$_{19}$FN$_2$O 334[M$^+$] |
| 8 k | i-C$_3$H$_7$ | 4-C$_6$H$_4$CH$_3$ | 4-C$_6$H$_4$CH$_3$ | C$_{22}$H$_{22}$N$_2$O 330[M$^+$] |
| 8 l | i-C$_3$H$_7$ | 4-C$_6$H$_4$OCH$_3$ | 4-C$_6$H$_4$OCH$_3$ | C$_{22}$H$_{22}$N$_2$O$_3$ 362 [M$^+$] |
| 8 m | CH$_3$ | 4-FC$_6$H$_4$ | 4-FC$_6$H$_4$ | C$_{18}$H$_{12}$F$_2$N$_2$O 310 [M$^+$] |

TABLE 8-continued

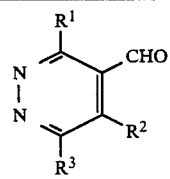

EXAMPLE 9

General procedure for the preparation of compounds of the general formula VI

Example 9a (R$^1$=i-C$_3$H$_7$, R$^2$=4-FC$_6$H$_4$, R$^3$=4-FC$_6$H$_4$, X-Y=CH=CH)

3,4-Di(4-fluorophenyl)-6-isopropylpyridazine-5-ethenyl cyanide

White oil is removed from 242 mg (5.6 mmol) of sodium hydride under argon, and 20 ml of THF are added. 0.9 ml (4.6 mmol) of diisopropyl cyanomethanephosphonate is injected at 0° C. After evolution of gas has ceased (about 30 minutes) 1.3 g (4 mmol) of the compound from Example 8a in 20 ml of THF are added dropwise, and the mixture is stirred at room temperature for 3 hours. The mixture is poured onto saturated NaCl solution and extracted 3 x with ether. The combined organic phases are washed once with saturated NaCl solution and dried (MgSO$_4$). Removal of the solvent in vacuo and chromatography on silica gel (cyclohexane/ethyl acetate 1/1) yields 985 mg of a white solid (title compound).

Melting point: 160° C.
MS, C$_{22}$H$_{17}$F$_2$N$_3$=361 (M$^+$).
$^1$H-NMR δ/ppm=1.50 (d,J=7 Hz,6H); 3.40 (h,1H); 5.33 (d,J=16 Hz,1H); 6.83-7.55 (m,8H).

The examples in Table 9 were obtained in analogy to Example 9a.

TABLE 9

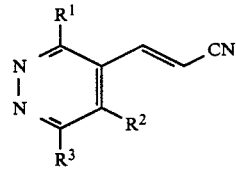

| Example | R$^1$ | R$^2$ | R$^3$ | Moss. mass |
|---|---|---|---|---|
| 9 b | CH$_3$ | 4-FC$_6$H$_4$ | C$_6$H$_5$ | C$_{20}$H$_{14}$FN$_3$ 315[M$^+$] |
| 9 c | CH$_3$ | C$_6$H$_5$ | C$_6$H$_5$ | C$_{20}$H$_{15}$N$_3$ 297[M$^+$] |
| 9 d | i-C$_3$H$_7$ | CH$_3$ | C$_6$H$_5$ | C$_{17}$H$_{17}$N$_3$ 263[M$^+$] |
| 9 e | i-C$_3$H$_7$ | 4-FC$_6$H$_4$ | i-C$_3$H$_7$ | C$_{19}$H$_{20}$FN$_3$ 309[M$^+$] |
| 9 f | i-C$_3$H$_7$ | 4-FC$_6$H$_4$ | c-C$_6$H$_{11}$ | C$_{22}$H$_{24}$FN$_3$ 349[M$^+$] |
| 9 g | 4-FC$_6$H$_4$ | i-C$_3$H$_7$ | C$_6$H$_5$ | C$_{22}$H$_{18}$FN$_3$ 343[M$^+$] |
| 9 h | 4-FC$_6$H$_4$ | i-C$_3$H$_7$ | i-C$_3$H$_7$ | C$_{19}$H$_{20}$FN$_3$ 309[M$^+$] |
| 9 i | t-C$_4$H$_9$ | 4-FC$_6$H$_4$ | C$_6$H$_5$ | C$_{23}$H$_{20}$FN$_3$ |

TABLE 9-continued

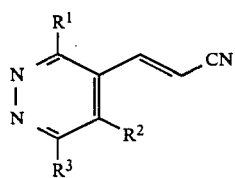

| Example | R¹ | R² | R³ | Moss. mass |
|---|---|---|---|---|
| 9 k | i-C₃H₇ | 4-C₆H₄CH₃ | 4-C₆H₄CH₃ | 357[M⁺] $C_{24}H_{23}N_3$ |
| 9 l | i-C₃H₇ | 4-C₆H₄OCH₃ | 4-C₆H₄OCH₃ | 353[M⁺] $C_{24}H_{23}N_3O_2$ |
| 9 m | CH₃ | 4-FC₆H₄ | 4-FC₆H₄ | 385 [M⁺] $C_{20}H_{13}F_2N_3$ 357 [M⁺] |

EXAMPLE 10

General procedure for the preparation of compounds of the general formula III

Example 10a (R¹=i-C₃H₇, R²=4-FC₆H₄, R³=4-FC₆H₄, X-Y=CH=CH)

3,4-Di(4-fluorophenyl)-6-isopropylpyridazine-5-propenal 4.5 ml (5.4 mmol) of diisobutylaluminum hydride solution (in toluene) are injected, at 0° C., into 975 mg (2.7 mmol) of the compound from Example 9a in 20 ml of THF. After 4 hours at 10° C., the mixture is cautiously hydrolyzed with 1N hydrochloric acid and extracted with ethyl acetate (3 x). The combined organic phases are washed once with saturated sodium bicarbonate solution and dried (MgSO₄). Removal of the solvent in vacuo and flash chromatography on silica gel (cyclohexane/ethyl acetate 1/1) yields 600 mg of a colorless oil (title compound).

MS, $C_{22}H_{18}F_2N_2O = 365$ (M⁺)

¹H-NMR: δ/ppm=1.57 (d,J=7 Hz,6H); 3.47 (h,1H); 6.20 (dd,J₁=16 Hz,J₂=7 Hz,1H); 6.77–7.60 (m,8H); 9.60 (d,J=7 Hz,1H).

The examples in Table 10 were obtained in analogy to Example 10a.

TABLE 10

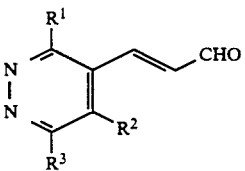

| Example | R¹ | R² | R³ | Mol. mass |
|---|---|---|---|---|
| 10 b | CH₃ | 4-FC₆H₄ | C₆H₅ | $C_{20}H_{15}FN_2O$ 318[M⁺] |
| 10 c | CH₃ | C₆H₅ | C₆H₅ | $C_{20}H_{16}N_2O$ 300[M⁺] |
| 10 d | i-C₃H₇ | CH₃ | C₆H₅ | $C_{17}H_{18}N_2O$ |

TABLE 10-continued

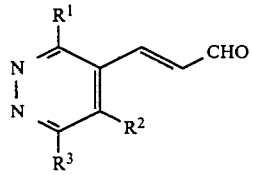

| Example | R¹ | R² | R³ | Mol. mass |
|---|---|---|---|---|
| 10 e | i-C₃H₇ | 4-FC₆H₄ | i-C₃H₇ | 266[M⁺] $C_{19}H_{21}FN_2O$ |
| 10 f | i-C₃H₇ | 4-FC₆H₄ | c-C₆H₁₁ | 312[M⁺] $C_{22}H_{25}FN_2O$ |
| 10 g | 4-FC₆H₄ | i-C₃H₇ | C₆H₅ | 352[M⁺] $C_{22}H_{19}FN_2O$ |
| 10 h | 4-FC₆H₄ | i-C₃H₇ | i-C₃H₇ | 346[M⁺] $C_{19}H_{21}FN_2O$ |
| 10 i | t-C₄H₉ | 4-FC₆H₄ | C₆H₅ | 312[M⁺] $C_{23}H_{21}FN_2O$ |
| 10 k | i-C₃H₇ | 4-C₆H₄CH₃ | 4-C₆H₄CH₃ | 360[M⁺] $C_{24}H_{24}N_2O$ |
| 10 l | i-C₃H₇ | 4-C₆H₄OCH₃ | 4-C₆H₄OCH₃ | 356[M⁺] $C_{24}H_{24}N_2O_3$ |
| 10 m | CH₃ | 4-FC₆H₄ | 4-FC₆H₄ | 388 [M⁺] $C_{20}H_{14}F_2N_2O$ 336 [M⁺] |

EXAMPLE 11

General procedure for the preparation of compounds of the general formula IV

Example 11a (R¹=i-C₃H₇, R²=4-FC₆H₄, R³=4-FC₆H₄, X-Y=CH=CH, R⁴=C₂H₅)

Ethyl 7-[3,4-di(4-fluorophenyl)-6-isopropylpyridazin-5-yl]-5-hydroxy-3-oxo-6-heptenoate 96 mg (2.2 mmol) of sodium hydride from which white oil has been removed are introduced under argon into 3 ml of dry THF. At 0° C., 265 μl (2.8 mmol) of ethyl acetate are injected, and the mixture is stirred at 0° C. for 15 minutes. Then 1.3 ml (2.0 mmol) of BuLi (hexane) are injected in at 0° C. After stirring for 15 minutes, 500 mg (1.4 mmol) of the compound from Example 10a in 5 ml of THF are added dropwise at −70° C., and the mixture is stirred at −70° C. for 2.5 hours. It is allowed to reach 0° C., hydrolyzed with cold 2N hydrochloric acid and extracted 3 x with ether. The combined organic extracts are washed once with saturated sodium chloride solution and dried (MgSO₄). Removal of the solvent in vacuo yields 650 mg of Example 11a.

The compound of Example 11a is used for the next stage without further purification and characterization. Oil

MS, $C_{28}H_{28}F_2N_2O_4 = 495$ (M⁺).

¹H-NMR: Compound is used in Example 12a without further characterization.

The examples in Table 11 were obtained in analogy to Example 11a.

TABLE 11

$$\text{structure: pyridazine with } R^1, R^2, R^3 \text{ substituents, and side chain } -CH=CH-CH(OH)-CH_2-C(O)-CH_2-CO_2R^4$$

| Example | $R^1$ | $R^2$ | $R^3$ | $R^4$ | Mol. mass |
|---|---|---|---|---|---|
| 11 b | $CH_3$ | $4\text{-}FC_6H_4$ | $C_6H_5$ | $C_2H_5$ | $C_{26}H_{25}FN_2O_4$ 448[M$^+$] |
| 11 c | $CH_3$ | $C_6H_5$ | $C_6H_5$ | $C_2H_5$ | $C_{26}H_{26}N_2O_4$ 430[M$^+$] |
| 11 d | $i\text{-}C_3H_7$ | $CH_3$ | $C_6H_5$ | $C_2H_5$ | $C_{23}H_{28}N_2O_4$ 396[M$^+$] |
| 11 e | $i\text{-}C_3H_7$ | $4\text{-}FC_6H_4$ | $i\text{-}C_3H_7$ | $C_2H_5$ | $C_{25}H_{31}FN_2O_4$ 442[M$^+$] |
| 11 f | $i\text{-}C_3H_7$ | $4\text{-}FC_6H_4$ | $c\text{-}C_6H_{11}$ | $C_2H_5$ | $C_{28}H_{35}FN_2O_4$ 482[M$^+$] |
| 11 g | $4\text{-}FC_6H_4$ | $i\text{-}C_3H_7$ | $C_6H_5$ | $C_2H_5$ | $C_{28}H_{29}FN_2O_4$ 476[M$^+$] |
| 11 h | $4\text{-}FC_6H_4$ | $i\text{-}C_3H_7$ | $i\text{-}C_3H_7$ | $C_2H_5$ | $C_{25}H_{31}FN_2O_4$ 442[M$^+$] |
| 11 i | $t\text{-}C_4H_9$ | $4\text{-}FC_6H_4$ | $C_6H_5$ | $C_2H_5$ | $C_{29}H_{31}FN_2O_4$ 490[M$^+$] |
| 11 k | $i\text{-}C_3H_7$ | $4\text{-}C_6H_4CH_3$ | $4\text{-}C_6H_4CH_3$ | $C_2H_5$ | $C_{30}H_{34}N_2O_4$ 486[M$^+$] |
| 11 l | $i\text{-}C_3H_7$ | $4\text{-}C_6H_4OCH_3$ | $4\text{-}C_6H_4OCH_3$ | $C_2H_5$ | $C_{30}H_{34}N_2O_6$ 518[M$^+$] |
| 11 m | $CH_3$ | $4\text{-}FC_6H_4$ | $4\text{-}FC_6H_4$ | $C_2H_5$ | $C_{26}H_{24}F_2N_2O_4$ 466[M$^+$] |

EXAMPLE 12

General procedure for the preparation of compounds of the general formula I

Example 12a, ($R^1 = i\text{-}C_3H_7$, $R^2 = 4\text{-}FC_6H_4$, $R^3 = 4\text{-}FC_6H_4$, $R^4 = C_2H_5$, X-Y=CH=CH)

Ethyl 7-[3,4-di(4-fluorophenyl)-6-isopropylpyridazin-5-yl]-3,5-dihydroxy-6-heptenoate 140 mg (0.3 mmol) of the compound from Example 11a are dissolved under argon in 4 ml of dry THF, 0.4 ml (0.4 mmol) of triethylborane solution (THF) is added, and the mixture is stirred at room temperature for 10 minutes. At −70° C., 21.4 mg (0.6 mmol) of solid sodium borohydride are added. Subsequently 3 ml of methanol are slowly injected. After 3 h at −70° C., the mixture is poured onto to a cooled solution of 0.5 ml of 35% hydrogen peroxide in 4.4 ml of water. After 5 minutes the mixture is extracted with ethyl acetate (3 x). The combined organic phases are washed with saturated sodium bicarbonate solution (2 x) and saturated brine (1 x) and dried (MgSO$_4$). Removal of the solvent in vacuo and flash chromatography on silica gel (cyclohexane/ethyl acetate 1/1+0.5% Et$_3$N) yields 91 mg of Example 12a.

Melting point: 85° C.

MS, $C_{28}H_{30}F_2N_2O_4 = 496$ (M+H$^+$).

$^1$H-NMR: δ/ppm=1.29 (tr,J=7 Hz,3H); 1.47 (d,6H); 1.43 (m,2H); 2.44 (m,2H); 3.50 (h,1H); 4.15 (m,1H); 4.20 (q,2H); 4.40 (m,1H); 5.46 (dd,J$_1$=16 Hz, J$_2$=7 Hz,1H); 6.50 (d,J=16 Hz,1H); 6.87–7.34 (m,8H).

The examples in Table 12 were obtained in analogy to Example 12a.

TABLE 12

$$\text{structure: pyridazine with } R^1, R^2, R^3 \text{ substituents, side chain } -CH=CH-CH(OH)-CH_2-CH(OH)-CH_2-CO_2R^4$$

| Example | $R^1$ | $R^2$ | $R^3$ | $R^4$ | Mol. mass |
|---|---|---|---|---|---|
| 12 b | $CH_3$ | $4\text{-}FC_6H_4$ | $C_6H_5$ | $C_2H_5$ | $C_{26}H_{27}FN_2O_4$ 450[M$^+$] |
| 12 c | $CH_3$ | $C_6H_5$ | $C_6H_5$ | $C_2H_5$ | $C_{26}H_{28}N_2O_4$ 432[M$^+$] |
| 12 d | $i\text{-}C_3H_7$ | $CH_3$ | $C_6H_5$ | $C_2H_5$ | $C_{23}H_{30}N_2O_4$ 398[M$^+$] |
| 12 e | $i\text{-}C_3H_7$ | $4\text{-}FC_6H_4$ | $i\text{-}C_3H_7$ | $C_2H_5$ | $C_{25}H_{33}FN_2O_4$ 444[M$^+$] |
| 12 f | $i\text{-}C_3H_7$ | $4\text{-}FC_6H_4$ | $c\text{-}C_6H_{11}$ | $C_2H_5$ | $C_{28}H_{37}FN_2O_4$ 484[M$^+$] |
| 12 g | $4\text{-}FC_6H_4$ | $i\text{-}C_3H_7$ | $C_6H_5$ | $C_2H_5$ | $C_{28}H_{31}FN_2O_4$ 478[M$^+$] |
| 12 h | $4\text{-}FC_6H_4$ | $i\text{-}C_3H_7$ | $i\text{-}C_3H_7$ | $C_2H_5$ | $C_{25}H_{33}FN_2O_4$ |

TABLE 12-continued

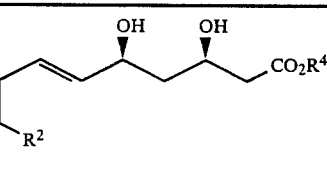

| Example | $R^1$ | $R^2$ | $R^3$ | $R^4$ | Mol. mass |
|---|---|---|---|---|---|
| 12 i | $t\text{-}C_4H_9$ | $4\text{-}FC_6H_4$ | $C_6H_5$ | $C_2H_5$ | $C_{29}H_{33}FN_2O_4$ 444[M+] |
| 11 k | $i\text{-}C_3H_7$ | $4\text{-}C_6H_4CH_3$ | $4\text{-}C_6H_4CH_3$ | $C_2H_5$ | $C_{30}H_{36}N_2O_4$ 492[M+] |
| 12 l | $i\text{-}C_3H_7$ | $4\text{-}C_6H_4OCH_3$ | $4\text{-}C_6H_4OCH_3$ | $C_2H_5$ | $C_{30}H_{36}N_2O_6$ 488[M+] |
| 12 m | $CH_3$ | $4\text{-}FC_6H_4$ | $4\text{-}FC_6H_4$ | $C_2H_5$ | $C_{26}H_{26}F_2N_2O_4$ 520[M+] 468[M+] |

EXAMPLE 13

General procedure for the preparation of compounds of the general formula I

Example 13a ($R^1 = i\text{-}C_3H_7$, $R^2 = 4\text{-}FC_6H_4$, $R^3 = 4\text{-}FC_6H_4$, $R^4 = Na$, X-Y=CH=CH)

Sodium 7-[3,4-di(4-fluorophenyl)-6-isopropylpyridazin-5-yl]-3,5-dihydroxy-6-heptenoate 42 mg (0.09 mmol) of the compound from Example 12a are dissolved in 2 ml of ethanol, and 0.9 ml (0.09 mmol) of 0.1N sodium hydroxide solution is added. After 1 hour at room temperature, the solvent is removed in vacuo, adding toluene several times. The solid residue is washed several times with n-pentane and dried under high vacuum.

The examples in Table 13 were obtained in analogy to Example 13a.

TABLE 13

| Example | $R^1$ | $R^2$ | $R^3$ | Mol. mass |
|---|---|---|---|---|
| 13 b | $CH_3$ | $4\text{-}FC_6H_4$ | $C_6H_5$ | $C_{24}H_{22}FN_2O_4Na$ 444[M+] |
| 13 c | $CH_3$ | $C_6H_5$ | $C_6H_5$ | $C_{24}H_{23}N_2O_4Na$ 426[M+] |
| 13 d | $i\text{-}C_3H_7$ | $CH_3$ | $C_6H_5$ | $C_{21}H_{25}N_2O_4Na$ 376[M+] |
| 13 e | $i\text{-}C_3H_7$ | $4\text{-}FC_6H_4$ | $i\text{-}C_3H_7$ | $C_{23}H_{28}FN_2O_4Na$ 438[M+] |
| 13 f | $i\text{-}C_3H_7$ | $4\text{-}FC_6H_4$ | $c\text{-}C_6H_{11}$ | $C_{26}H_{32}FN_2O_4Na$ 478[M+] |
| 13 g | $4\text{-}FC_6H_4$ | $i\text{-}C_3H_7$ | $C_6H_5$ | $C_{26}H_{26}FN_2O_4Na$ 472[M+] |
| 13 h | $4\text{-}FC_6H_4$ | $i\text{-}C_3H_7$ | $i\text{-}C_3H_7$ | $C_{23}H_{28}FN_2O_4Na$ 438[M+] |
| 13 i | $t\text{-}C_4H_9$ | $4\text{-}FC_6H_4$ | $C_6H_5$ | $C_{27}H_{28}FN_2O_4Na$ 486[M+] |
| 13 k | $i\text{-}C_3H_7$ | $4\text{-}C_6H_4CH_3$ | $4\text{-}C_6H_4CH_3$ | $C_{28}H_{31}N_2O_4Na$ 482[M+] |
| 13 l | $i\text{-}C_3H_7$ | $4\text{-}C_6H_4OCH_3$ | $4\text{-}C_6H_4OCH_3$ | $C_{28}H_{31}N_2O_6Na$ 514[M+] |
| 13 m | $CH_3$ | $4\text{-}FC_6H_4$ | $4\text{-}FC_6H_4$ | $C_{24}H_{21}F_2N_2O_4Na$ 462[M+] |

EXAMPLE 14

General procedure for the preparation of compounds of the general formula I

Example 14a ($R^1 = i\text{-}C_3H_7$, $R^2 = 4\text{-}FC_6H_4$, $R^3 = 4\text{-}FC_6H_4$, X-Y=CH=CH)

6-(2-(3,4-Di(4-fluorophenyl)-6-isopropylpyridazin-5-yl)ethenyl)-4-hydroxy-3,4,5,6-tetrahydro-2H-pyran-2-one 10 mg (0.02 mmol) of the compound from Example 12a are stirred with 9.3 µl (0.1 mmol) of trifluoroacetic acid in 1 ml of absolute dichloromethane at room temperature for 12 hours. The solution is concentrated and dried under high vacuum. Flash chromatography on silica gel (ethyl acetate) yields 9 mg of the title compound as a colorless oil.

MS, $C_{26}H_{24}F_2N_2O_3 = 450$ (M+)

$^1$H-NMR: δ/ppm = 1.44 (d,J=7 Hz,6H); 1.52–1.93 (m,3H); 2.61–2.84 (m,2H); 3.45 (h,J=7 Hz,1H); 5.20 (m,1H); 5.50 (dd,$J_1$=16 Hz, $J_2$=7 Hz,1H); 6.52 (d,J=16 Hz,1H); 7.00–7.41,(m,8H).

The examples in Table 14 are obtained in analogy to Example 14a.

TABLE 14

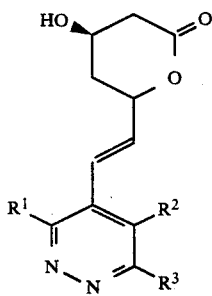

| Ex-ample | R¹ | R² | R³ | Mol. mass |
|---|---|---|---|---|
| 14 b | $CH_3$ | $4\text{-}FC_6H_4$ | $C_6H_5$ | $C_{24}H_{21}FN_2O_3$ 404[M+] |
| 14 c | $CH_3$ | $C_6H_5$ | $C_6H_5$ | $C_{24}H_{22}N_2O_3$ 386[M+] |
| 14 d | $i\text{-}C_3H_7$ | $CH_3$ | $C_6H_5$ | $C_{21}H_{24}N_2O_3$ 352[M+] |
| 14 e | $i\text{-}C_3H_7$ | $4\text{-}FC_6H_4$ | $i\text{-}C_3H_7$ | $C_{23}H_{27}FN_2O_3$ 398[M+] |
| 14 f | $i\text{-}C_3H_7$ | $4\text{-}FC_6H_4$ | $c\text{-}C_6H_{11}$ | $C_{26}H_{31}FN_2O_3$ 438[M+] |
| 14 g | $4\text{-}FC_6H_4$ | $i\text{-}C_3H_7$ | $C_6H_5$ | $C_{26}H_{25}FN_2O_3$ 432[M+] |
| 14 h | $4\text{-}FC_6H_4$ | $i\text{-}C_3H_7$ | $i\text{-}C_3H_7$ | $C_{23}H_{27}FN_2O_3$ 398[M+] |
| 14 i | $t\text{-}C_4H_9$ | $4\text{-}FC_6H_4$ | $C_6H_5$ | $C_{27}H_{27}FN_2O_3$ 446[M+] |
| 14 k | $i\text{-}C_3H_7$ | $4\text{-}C_6H_4CH_3$ | $4\text{-}C_6H_4CH_3$ | $C_{28}H_{30}N_2O_3$ 442[M+] |
| 14 l | $i\text{-}C_3H_7$ | $4\text{-}C_6H_4OCH_3$ | $4\text{-}C_6H_4OCH_3$ | $C_{28}H_{30}N_2O_5$ 474[M+] |
| 14 m | $CH_3$ | $4\text{-}FC_6H_4$ | $4\text{-}FC_6H_4$ | $C_{24}H_{20}F_2N_2O_3$ 422[M+] |

NMR spectra of compounds according to Example 14

Example 14b

¹H-NMR: δ/ppm=1.54–1.90 (m, 3H); 2.65–2.80 (m, 2H); 2.72 (s, 3H); 5.21 (m, 1H); 5.52 (dd,$J_1$=16 Hz, $J_2$=7 Hz,1H); 6.50 (d, J=16 Hz, 1H); 7.0–7.4 (m, 10H).

Example 14l

¹H-NMR: δ/ppm=1.42 (d, J=7 Hz, 6H); 1.53–1.93 (m, 3H); 2.61–2.84 (m, 2H); 3.44 (h, J=7 Hz, 1H); 3.90 (s, 6H); 5.21 (m, 1H); 5.52 (dd, $J_1$=16 Hz, $J_2$=7 Hz, 1H); 6.52 (d, J=16 Hz; 1H); 7.0–7.4 (m, 8H).

Example 14m

¹H-NMR: δ/ppm=ppm=1.53–1.89 (m, 3H); 2.63–2.75 (m, 2H); 2.77 (s, 3H); 5.20 (m, 1H); 5.50 (dd, $J_1$=16 Hz, $J_2$=7 Hz, 1H); 6.52 (d, J=16 Hz, 1H); 7.0–7.4 (m, 8H).

Example 15

General procedure for the preparation of compounds of the general formula V (optically active)

Example 15a ($R^1$=i-$C_3H_7$, $R^2$=4-$FC_6H_4$, $R^3$=4-$FC_6H_4$,
$R^5$=CH($C_6H_5$)—C(OH)($C_6H_5$)$_2$, X-Y =CH=CH)
(S)-(−)-2-hydroxy-1,2,2-triphenylethyl
5-[3,4-di(4-fluorophenyl)-6-isopropylpyridazin-5-yl]-3(S)-hydroxy-4(E)-pentenoate A 1.6M solution of n-butyllithium in hexane (150 ml; 240 mmol) is slowly added dropwise to a solution of diisopropylamine (33.6 ml; 240 mmol) in 400 ml of absolute THF at −78° C. This solution is stirred at 0° C. for 30 minutes and then, at −78° C., (S)-(−)-2-hydroxy-1,2,2-triphenyl-ethyl acetate (35.5 g; 107 mmol) is added in portions.

The mixture is stirred for 30 minutes, and the temperature is raised to 0° C. until a red solution is produced. The solution is cooled again to −78° C.

In another flask, 5.5 g (224 mmol) of magnesium turnings are covered with 100 ml of absolute THF. Dibromoethane (41.3 g; 220 mmol) is now added dropwise in such a way that the solution boils gently. After the addition is complete, the solution is cooled to −78° C. and slowly added dropwise, using a transfer needle, to the solution prepared above. A solution of 39.2 g (107 mmol) of aldehyde from Example 10a in 200 ml of THF, which has been pre-cooled to −78° C., is now added dropwise, using a transfer needle, to the solution prepared above, and the mixture is stirred at −78° C. for 1 hour. The cooled mixture is poured into a saturated ammonium chloride solution (500 ml) and stirred for 30 minutes (pH 8, 0° C.). The organic phase is separated off, and the aqueous phase is extracted with ether. The combined organic phases are washed with sodium chloride solution and dried over magnesium sulfate. Evaporation of the solvent yields 48.2 g of Example 15a as pale crystals.

The compound of Example 15a is used for the next stage without further purification.

Melting point: 80°–85° C.

MS, $C_{44}H_{38}F_2N_2O_4$=697 (M+H+).

¹H-NMR: δ/ppm=1.40 (d,J=7 Hz,6H); 1.53 (s,1H); 2.04 (s,1H); 2.23 (d,2H); 3.38 (h,1H); 4.35 (m,1H); 5.35 (dd,$J_1$=16 Hz,$J_2$=7 Hz,1H); 6.37 (dd,$J_1$=16 Hz,$J_2$=1.5 Hz,1H); 6.70–7.55 (m,23H).

EXAMPLE 16

General procedure for the preparation of compounds of the general formula V (optically active; methyl ester)

Example 16a ($R^1$=i-$C_3H_7$, $R^2$=4-$FC_6H_4$, $R^3$=4-$FC_6H_4$, $R^5$=$CH_3$, X-Y=CH=CH)

Methyl 5-[3,4-di(4-fluorophenyl)-6-isopropylpyridazin-5-yl]-3(S)-hydroxy-4(E)-pentenoate A solution of 80.5 mg of sodium (3.5 mmol) in 25 ml of absolute methanol is slowly added dropwise at 20° C. to a solution of 2 g (2.9 mmol) of ester from Example 15a in 100 ml of absolute methanol. The mixture is stirred at room temperature for 1 hour, and then neutralized with glacial acetic acid and evaporated. The residue is taken up in water and ether, 100 ml of each; the phases are separated, and the organic phase is washed with saturated sodium bicarbonate solution. After drying with magnesium sulfate, the solvent is removed in vacuo. The residue is chromatographed (cyclohexane/ethyl acetate 1/1) and yields 1.0 g of a crystalline solid.

Melting point: 125°–127° C.

MS, $C_{25}H_{24}F_2N_2O_3$=439 (M+H+).

¹H-MNR: δ/ppm=1.44 (d,J=7 Hz,6H); 1.58 (s,1H); 2.32 (m,2H); 3.43 (h,1H); 3.70 (s,3H); 4.50 (m,1H); 5.48 (dd,$J_1$=16 Hz,$J_2$=7 Hz,1H); 6.50 (dd,$J_1$=16 Hz,$J_2$=1.5 Hz,1H); 6.88–7.41 (m,(8H).

EXAMPLE 17

General procedure for the preparation of compounds of the general formula IV (optically active)

Example 17a ($R^1$=i-$C_3H_7$, $R^2$=4-$FC_6H_4$, $R^3$=4-$FC_6H_4$, X-Y=CH=C-H, $R^4$=t-butyl)

tert.-Butyl 7-[3,4-di(4-fluorophenyl)-6-isopropylpyridazin-5-yl]-5(S)-hydroxy-3-oxo-6(E)-heptenoate Under an argon atmosphere and at 0° C., 17.7 ml (28 mmol) of n-butyllithium (1.6M solution in hexane) are added dropwise to 4 ml (28 mmol) of diisopropylamine in 100 ml of absolute THF, and the mixture is stirred at 0° C. for 30 minutes. It is cooled to −40° C. and 3.8 ml (28 mmol) of tert.-butyl acetate are added dropwise. After 1 hour at −40° C., the methyl ester from Example 16a (3.1 g, 7.2 mmol), dissolved in 25 ml of THF, is added dropwise at this temperature, and the mixture is stirred at −20° C. for 1 hour. The cold solution is poured onto saturated ammonium chloride solution, the organic phase is separated off and then washed with sodium chloride solution and dried over magnesium sulfate, and the solvent is evaporated off in vacuo.

The residue is chromatographed on silica gel (cyclohexane/ethyl acetate 1/1) and yields Example 17a as a colorless oil.

MS, $C_{30}H_{32}F_2N_2O_4$=523 (M+$H^+$).

$^1$H-NMR: δ/ppm=1.48 (d+s,15H); 2.53 (m,2H); 3.32 (s,2H); 3.44 (h,1H); 4.57 (m,1H); 5.45 (dd,$J_1$=16 Hz,$J_2$=7 Hz,1H); 6.50 (dd,$J_1$=16 Hz, $J_2$=1.5 Hz,1H); 6.88-7.32 (m,8H).

EXAMPLE 18

General procedure for the preparation of compounds of the general formula I (optically active)

Example 18a ($R^1$=i-$C_3H_7$, $R^2$=4-$FC_6H_4$, $R^3$=4-$FC_6H_4$, $R^1$=tert.-butyl, X-Y=CH=CH)

tert.-Butyl 7-[3,4-di(4-fluorophenyl)-6-isopropylpyridazin-5-yl]-3(R),5(S)-dihydroxy-6(E)-heptenoate The general procedure corresponds to the procedure of Example 12a.

Oil.

MS, $C_{30}H_{34}F_2N_2O_4$=525 (M+$H^+$).

$^1$H-NMR: δ/ppm=1.45 (d+s,15H); 1.55 (m,2H); 2.32 (d,2H); 3.45 (h,1H); 3.64 (s,1H); 3.78 (S,1H); 4.08 (m,1H); 4.37 (m,1H); 5.39 (dd,1H); 6.44 (dd,1H); 6.85-7.27 (m,8H)

EXAMPLE 19

General procedure for the preparation of compounds of the general formula I (optically active)

Example 19a ($R^1$=i-$C_3H_7$, $R^2$=4-$FC_6H_4$, $R^3$=4-$FC_6H_4$, $R^4$=Na, X-Y=CH=CH)

Sodium 7-[3,4-di(4-fluorophenyl)-6-isopropylpyridazin-5-yl]-3(R),5(S)-dihydroxy-6(E)-heptenoate The general procedure corresponds to the procedure of Example 13a.

Melting point: >230° C.

$^1$H-NMR ($D_2O$): δ/ppm=1.44 (d,6H); 1.62 (m,2H); 2.28 (d,2H); 3.60 (h,1H); 4.33 (m,1H); 4.80 (m,1H); 5.64 (dd,1H); 6.60 (dd,1H); 7.03-7.36 (m,8H).

We claim:

1. 3,5-Dihydroxy carboxylic acids and derivatives thereof, of the formula I

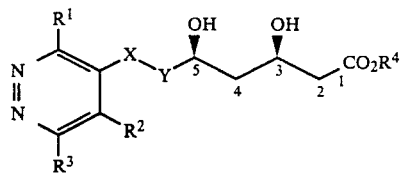

and the corresponding lactones of the formula II

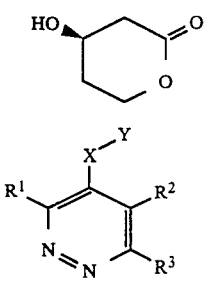

where, in the general formulae I and II, X-Y denotes a radical of the formula —CH=CH— or —$CH_2$—$CH_2$—

$R^1$, $R^2$ and $R^3$ denote, independently of one another hydrogen, a saturated or unsaturated, straight-chain or branched hydrocarbon radical which has up to 6 carbon atoms and can optionally be substituted on the terminal carbon by a saturated or unsaturated, cyclic hydrocarbon radical having 3 to 6 carbon atoms, or denote a cyclic, saturated or up to doubly unsaturated hydrocarbon radical having 3 to 7 carbon atoms, an aromatic radical selected from phenyl, furyl, thienyl and pyridyl, which can optionally carry in the nucleus 1 to 3 identical or different substituents selected halogen trifluoromethyl, alkyl and alkenyl, having up to 6 carbon atoms in each case, hydroxyl, alkoxy having 1 to 6 carbon atoms, carboxyl or carbalkoxy having 1 to 6 carbon atoms in the alkoxy moiety, $R^4$ denotes hydrogen, a straight-chain or branched, saturated or unsaturated hydrocarbon radical having up to 8 carbon atoms, mono- or dihydroxyalkyl having 1 to 4 carbon atoms, a phenyl or benzyl radical whose nuclei can be substituted once or twice by halogen or an alkyl radical having 1 to 4 carbon atoms, or denotes alkali metal or an ammonium ion.

2. Compounds of the general formulae I and II as claimed in claim 1, wherein $R^1$ and $R^2$ denote a straight-chain or branched alkyl radical having 1 to 4 carbon atoms, a cycloalkyl radical having 5 to 6 carbon atoms, a cycloalkylmethyl or cycloalkenylmethyl radical having a ring size of 5 to 6 carbon atoms, a phenyl radical which can optionally carry 1 to 3 identical or different substituent selected halogen, trifluoroemthyl, alkyl having 1 to 4 carbon atoms, hydroxyl, alkoxy having 1 to 4 carbon atoms and carbalkoxy having 1 to 4 carbon atoms in the alkoxy moiety, $R^3$ denotes hydrogen, a straight-chain or branched alkyl or alkenyl radical having up to 6 carbon atoms, a cycloalkyl or cycloalkenyl radical each having 5 to 6 carbon atoms, a phenyl or pyridyl radical, it being possible for the aromatic radicals optionally to carry 1 to 3 identical or different substituents selected halogen, alkyl having 1 to 4 carbon atoms, hydroxyl, alkoxy having 1 to 4 carbon atoms and carbalkoxy having 1 to 4 carbon atoms in the alkoxy moiety, and $R^4$ represents hydrogen, methyl, ethyl, isopropyl, isobutyl, benzyl, sodium, potassium, ammonium ($NH_4$) or methyltris(hydroxymethyl)ammonium.

3. Compounds of the general formulae I and II as claimed in claim 1, wherein $R^1$ denotes methyl, iospropyl, sec.-butyl, tert.-butyl, cyclohexyl, phenyl, 4-chloro-phenyl, 4-fluorophenyl, 4-methoxyphenyl, 4-fluoro-3-methyl-phenyl, 3,5-dimethylphenyl, cyclohexylmethyl or 4-trifluoromethylphenyl, $R^2$ denotes methyl, isopropyl, sec.-butyl, tert.-butyl, cyclohexyl, phenyl, 4-chlorophenyl, 4-fluorophenyl, 4-methoxyphenyl, 4-fluoro-3-methylphenyl, 3,5-dimethylphenyl, cyclohexylmethyl or 4-trifluoromethylphenyl, $R^3$ denotes hydrogen, methyl, isopropyl, sec.-butyl, tert.-butyl, cyclohexyl, phenyl, 4-fluorophenyl, 2,5-dimethylphenyl, 3,5-dimethylphenyl or 4-trifluoromethylphenyl, and $R^4$ represents hydrogen, methyl, ethyl, sodium or potassium.

4. Compounds as claimed in claim 1, which have the formula I.

5. A pharmaceutical composition comprising an amount effective for use in the therapy of a mammal of a compound of the formula I as claimed in claim 1 together with a pharmaceutically acceptable carrier.

6. A method for the prophylaxis and therapy of hypercholesterolemia which comprises administering to a host an effective amount of a compound of the formula I as claimed in claim 1.

* * * * *

UNITED STATES PATENT AND TRADEMARK OFFICE
CERTIFICATE OF CORRECTION

PATENT NO. : 4,946,841

DATED : August 7, 1990

INVENTOR(S) : Ekkehard Baader et al

It is certified that error appears in the above-identified patent and that said Letters Patent is hereby corrected as shown below:

Claim 1, column 28, line 30, delete "general";

Claim 1, column 28, line 44, "selected" should be followed by --from,-- and "halogen" should be followed by --,--;

Claim 2, column 28, line 58, delete "general";

Claim 2, column 28, line 65, "substituent" should be --substitents-- and "selected" should be followed by --from--;

Claim 2, column 29, line 7, "selected" should be followed by --from--;

Claim 3, column 29, line 14, delete "general".

Signed and Sealed this

Eleventh Day of August, 1992

Attest:

DOUGLAS B. COMER

*Attesting Officer*  *Acting Commissioner of Patents and Trademarks*